United States Patent [19]

Park et al.

[11] Patent Number: 5,139,564
[45] Date of Patent: Aug. 18, 1992

[54] HERBICIDAL ARYLOXYACETIC ACID DERIVATIVES

[76] Inventors: Sang W. Park, 39-1, Hawolgok-Dong, Sungbuk-Ku, Seoul; Byung I. Lee, 1036-23, Doksan 2-Dong, Kuro-Ku, Seoul, both of Rep. of Korea

[21] Appl. No.: 637,383

[22] Filed: Jan. 3, 1991

Related U.S. Application Data

[60] Division of Ser. No. 467,313, Jan. 17, 1990, abandoned, which is a continuation of Ser. No. 285,293, Dec. 15, 1988, abandoned, which is a continuation of Ser. No. 831,081, Feb. 19, 1986, abandoned.

[30] Foreign Application Priority Data

Nov. 19, 1985 [KR] Rep. of Korea .................. 1985-8639

[51] Int. Cl.$^5$ ...................... A01N 43/40; A01N 43/50
[52] U.S. Cl. ............................................... 71/92; 71/94
[58] Field of Search .................. 71/92, 94; 546/309; 548/320

[56] References Cited

U.S. PATENT DOCUMENTS

| | | | |
|---|---|---|---|
| 3,445,221 | 5/1969 | Regel | 71/72 |
| 3,716,554 | 2/1970 | Little et al. | 548/320 |
| 4,535,087 | 8/1985 | Spatz | 546/309 |
| 4,608,081 | 8/1986 | Someya et al. | 546/309 |

FOREIGN PATENT DOCUMENTS

| | | | |
|---|---|---|---|
| 3101889 | 8/1982 | Fed. Rep. of Germany | 546/309 |
| 0770063 | 3/1957 | United Kingdom | 546/309 |

OTHER PUBLICATIONS

Chemical Abstracts, 73: 97857c.
Chemical Abstracts, 70:136,818m.
Chemical Abstracts, 81:59326m.
Chemical Abstracts, 94:208,559.
Chemical Abstracts: 94:208560.

*Primary Examiner*—Jane T. Fan
*Attorney, Agent, or Firm*—Townsend and Townsend

[57] ABSTRACT

Aryloxyacetic acid derivatives of the formula

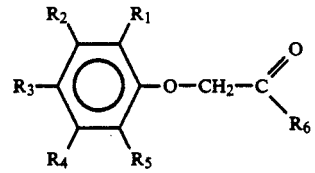

where $R_1$ is H, $CH_3$, Cl, Br, F, or $NO_2$; $R_2$ is H or Cl; $R_3$ is H, $CH_3 C(CH_3)_3$, Cl, Br or $NO_2$; $R_4$ is H or Cl; $R_5$ is H, $CH_3$, Cl, Br or F; and $R_6$ is 2-pyridylamino or 2-ethylene thiourea, are useful a herbicides.

3 Claims, No Drawings

HERBICIDAL ARYLOXYACETIC ACID DERIVATIVES

This is a division of application Ser. No. 07/467,313 filed Jan. 17, 1990, now abandoned which is a continuation of Ser. No. 07/285,293 filed Dec. 15, 1988, abandoned which is a continuation of Ser. No. 06/831,018 filed Feb. 19, 1986, now abandoned.

DETAILED EXPLANATIONS ON INVENTION

The present invention relates to novel aryloxyacetic acid derivatives of the below mentioned general formula(1) which are biologically active and useful in particular as herbicides.

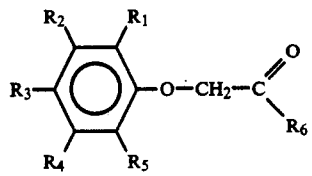

In the above mentioned general formula(1), $R_1$ is selected from among —H, —$CH_3$, —Cl, —Br, —F and $NO_2$, and $R_2$ represents —H or —Cl. $R_3$ is selected from among —H, —$CH_3$, —$C(CH_3)_3$, —Cl, —Br and —$NO_2$ while $R_4$ represents —H or —Cl. $R_5$ is selected from among —H, —$CH_3$, —Cl, —Br and —F, and $R_6$ is selected from among

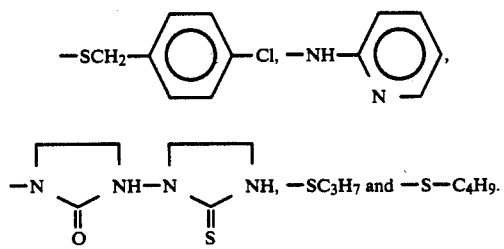

The compounds indicated by the above general formula(1) are related to such novel aryloxyacetic acid derivatives, including a process for their manufacture, as 2-(2',3'-dichlorophenoxy)-N-(2'-pyridinyl)acetamide, 2-(2',6'-(dichlorophenoxy)-N-(2'-pyridinyl)-acetamide, 2-(2',4',6'-trichlorophenoxy)-N-(2'-pyridinyl)-acetamide, 2-(2',4',5'-trichlorophenoxy)-N-(2'-pyridinyl)-acetamide, 2-(4'-bromo-2'-chlorophenoxy)-N-(2'-pyridinyl)-acetamide, 2-(4'-t-butylphenoxy)-N-(2'-pyridinyl)-acetamide, 2-(4'-chloro-2'-nitrophenoxy)-N-(2'-pyridinile)-acetamide, 2-(4'-bromo-2',6'-dimethylphenoxy)-N-(5'-chloro-2'-pyrididinyl)-acetamide, 2-(2',4',6'-trichlorophenoxy)-N-(5'-chloro-2'-pyrididinyl)-acetamide, 2-(2',6'-dibromo-4'-methylphenoxy)-N-(5'-chloro-2'-pyridinyl)-acetamide, 2-(4'-bromo-2',6'-dimethylphenoxy)-acet-S-propylester, 2-(2',6'-dichlorophenoxy)-acet-S-butylester, 2-(2',6'-dichlorophenoxy)-acet-S-(para-chlorobenzyl)-ester, 2-(2',4',5'-trichlorophenoxy)-acet-S-(para-chlorobenzyl)-ester, 2-(2',3'-dichlorophenoxy)-acet-S-(para-chlorobenzyl)-ester, 2-(4'-t-butylphenoxy)-acet-S-(para-chlorobenzyl)-ester, 2-(4'-bromo-2',6'-dimethylphenoxy)-N-(2'-pyridinyl)-acetamide, 2-(2',6'-dibromo-4'-methylphenoxy)-acet-S-(para-chlorobenzyl)-ester, 2-(2',4',6'-trichlorophenoxy)-acet-S-(para-chlorobenzyl)-ester, N-(2,5-dichlorophenoxyacetyl)-ethyleneurea, N-(2-chloro-4-nitrophenoxyacetyl)-ethyleneurea, N-(2-chloro-4-nitrophenoxyacetyl)-ethylene thiourea, N-(2,3-dichlorophenoxyacetyl)-ethylene thiourea, N-(2,6-difluorophenoxyacetyl)-ethylene thiourea and N-(3,4,5-trichlorophenoxyacetyl)-ethylene thiourea.

The novel compounds of the present invention as mentioned above are manufactured by the following three processes: Namely, in the first process, substituted phenol of the general formula (II) is reacted with monochloroacetic acid of the general formula(III) in the presence of bases to prepare aryloxyacetic acid of the general formula(IV).

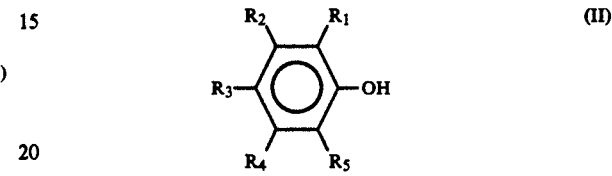

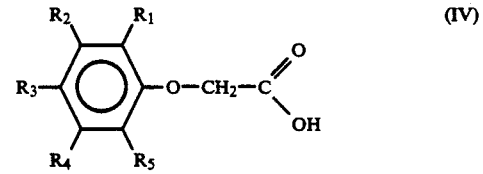

$R_1$, $R_2$, $R_3$, $R_4$ and $R_5$ in the above mentioned general formula(II) and general formula(IV) are the same as in the general formula(I).

In the second process, the compound of the general formula (IV) prepared by the first process is reacted with thionyl chloride of the general formula(V) in the presence or absence of an organic solvent to prepare aryloxyacetyl chloride of the general formula(VI).

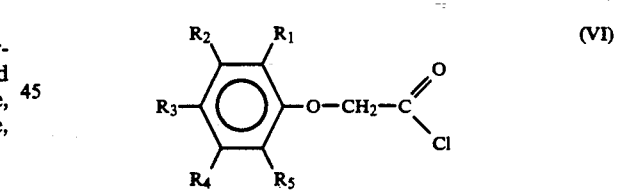

In the above general formula(VI), $R_1$, $R_2$, $R_3$, $R_4$ and $R_5$ are the same as in the general formula(I).

In the third process, the compound of the general formula (VI) prepared by the second process is reacted with 2-aminopyridine, 4-chlorobenzyl mercaptan, thyleneurea, propylene mercaptan and butyl mercaptan to manufacture the above-mentioned novel compounds.

Methods of manufacturing aryloxyacetic acid of the general formula(IV) have been published in many literatures, with some of them introduced as follows:

In Herbicide Handbook of the Weed Science Society of America, 2nd ed. Vol. 1 and 2, Residue Rev. 36 157(1971), Encyclopedia of Chemical Technology, 2nd ed. Vol. 22. pp. 179-183 and J. Am. Chem. Soc. 83, 3668(1961), halogen-substituted phenol of the general formula(II) was reaction with monochloroacetic acid of the general formula(III) in an alkaline aqueous solution to prepare aryloxyacetic acid of the general formula(IV). Meanwhile, in J. Am. Chem. Soc. 83 3668(1961), U.S. Pat. Nos. 2,471,575(1949) and 2,740,810(1956) is introduced the process of preparing aryloxyacetic acid of the general formula(IV) by the chlorination of phenoxyacetic acid or phenoxyacetic acid alkylester followed by subsequent hydrolysis.

Methods of manufacturing aryloxyacetyl chloride of the general formula(VI) have been published in many literatures, with a few of them introduced as follows:

J. Org. Chem 17 891(1952), Weeds 3 28(1954), J. Agr. Food Chem 4 140(1956), 12 434(1964) and J. Am. Chem. Soc. 88 3440 (1966) described that aryloxyacetic acid of the general formula (IV) was reacted with phosphorus pentachloride or thionyl chloride of the general formula(V) in the presence of bases to prepare aryloxyacetyl chloride of the general formula(VI).

As for 2-(aryloxy)-N-(2'-pyridinyl)-acetamide, a compound of the general formula(I), 2,5-dichloro-2-pyridineamine and 2,4-dichlorophenoxyacetyl chloride were reacted in toluene solvent in the presence of bases to prepare 2-(2,4-dichlorophenoxy)-N-(2',5'-dichloro-2'-pyridinyl)-acetamide in German Patent 3.101.889. Methods of manufacturing N-(aryloxyacetyl)-ethyleneurea and N-aryloxyacetyl)-ethylene thiourea, which are compounds of the general formula(I), have been published in a few papers. According to U.S. Pat. No. 2,740,810(1956), one of the methods calls for the reaction of aryloxyacetyl chloride with ethyleneurea in a nonactive solvent, for example trichloroethylene or carbon tetrachloride, in the presence of bases to synthesize N-(aryloxyacetyl)-ethyleneurea.

However, though similar to the present invention in their reaction principle, these methods are different in terms of reaction conditions, starting materials and final products.

Concrete explanations can be given as follows on the method of preparing the novel compound of the present invention:

In the first process, an important factor is proper selection of bases, temperature and solvents in synthesizing aryloxyacetic acid of the general formula(IV) by the reaction of substituted phenol of the general formula(II) with monochloroacetic acid. As bases, both sodium hydroxide and potassium hydroxide served to increase its yield. In other words, when the reaction is effected at the reflux temperature with the addition of these compounds, it is carried out in a short period of time. As solvents, there are alcohols and water but a better yield was obtained in water rather than alcohols. As for the temperature, the reaction time was reduced when it was 110°–120° C., also increasing the yield.

In the second process, aryloxyacetic acid of the general formula(IV) as synthesized above is reacted with thionyl chloride for further synthesis of aryloxyacetyl chloride of the general formula(VI). An important factor is the selection of proper solvents and reactants with no side reactions. The use of thionyl chloride both as solvent and reactant leads to a reaction with no side effects to be almost qualtitatively realized in a short period of time. Also, when anhydrous benzene or toluene is in use as a solvent, the reaction is realized in a satisfactory manner. When phosphorus pentachloride is used as a reactant, the reaction also proceeds but it is disadvantageous to commercialization due to quantities of toxic gases generated.

In the third process, such aryloxyacetic acid derivatives of the general formula(I) as aryloxyacet-N-2-pyridinileamide, aryloxythioester, aryloxyalkylester and aryloxybenzylester are synthesized. An important factor is the selection of catalysts, solvents and temperature. Triethylamine or pyridine is used as a catalyst, but pyridine has a disadvantage of difficulties in the disposal of pyridine hydrochloride as a byproduct. However, triethylamine increases the yield while shortening its reaction time. The disposal of triethylamine hydrochloride is also relatively easy. Anhydrous benzene and anhydrous toluene are in use as solvents. These compounds are good solvents, because they increase the solubility of the reaction mixture to effect the reaction in a short period of time.

In the reaction temperature, the reflux temperature of solvent accelerates an increase in yield. Since a lower temperature requires long hours, it is unfavorable from an economic standpoint.

As described in detail, the expected chemical reaction mechanism when manufacturing aryloxyacetic acid derivatives of the general formula(I) as novel compounds on the basis of the present invention is as follows:

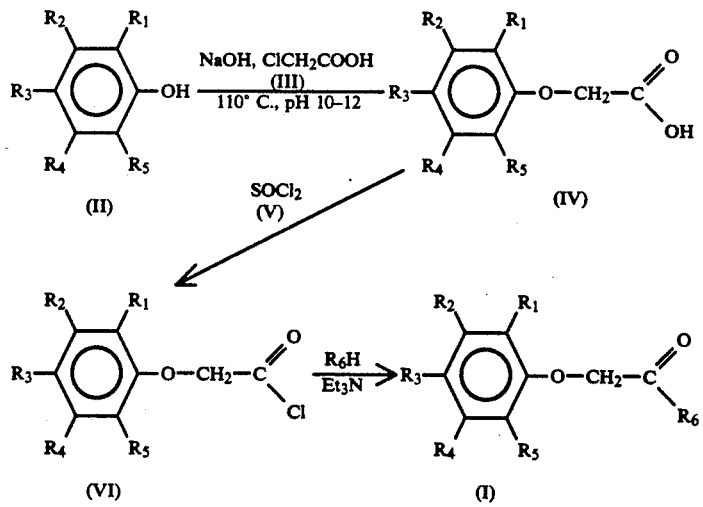

In the following examples, the present invention will be illustrated in more detail, but it is not limited hereto in its scope.

EXAMPLE 1

Manufacture of 2,4,6-trichlorophenoxyacetic acid 26.4 g (0.66 mol) of sodium hydroxide and 59.1 g (0.299 mol) of 2,4,6-trichlorophenol were respectively added to 450 ml of water for dissolution at normal temperature. Adding 28.11 g (0.299 mol) of monochloroacetic acid hereto, the reaction mixture was heated and refluxed for 9 to 10 hours, while the external temperature was maintained at 110°-120° C. On completion of the reaction, it was lowered to normal temperature to be followed by the filtration of product precipitate. The above reaction product was dissolved in 100 g of water and acidified with concentrated hydrochloric acid to obtain 70.5 g of 2,4,6-trichloropnenoxyacetic acid as a raw product.

When the above compound was recrystallized by 90 ml of benzene, 64.9 g of 2,4,6-trichlorophenoxyacetic acid as a target compound was obtained. The yield of the target compound in relation to 2,4,6-trichlorophenol consumed was 85 percent. Its melting point was 180°-183° C.

EXAMPLE 2

Manufacture of 2,4,6-trichlorophenoxyacetyl chloride

Filling in a dry 250 ml flask respectively 64.9 g (0.254 mol) of 2,4,6-trichlorophenoxyacetic acid synthesized in Example 1 and 74.4 ml (1.02 mol) of thionyl chloride, the reaction mixture was heated and refluxed for 5 to 6 hours.

When the reaction ended, the residual thionyl chloride was eliminated under reduced pressure to obtain 64.3 g of 2,4, 6-trichlorophenoxyacetyl chloride as a desired reaction product.

The yield of the target compound in relation to 2,4,6-trichlorophenoxyacetic acid consumed was 92.4 percent. The above compound requires to be completely sealed for use in the subsequent reaction.

EXAMPLE 3

Manufacture of 2-(2',4',6'-trichlorophenoxy)-N-(2'-pyridinyl)-acetamide

After filling in a dry 250 ml flask respectively 150 ml of anhydrous benzene and 32.45 g (0.118 mol) of 2,4,6-trichlorophenoxyacetyl chloride synthesized in Example 2, 11.11 g (0.118 mol) of 2-aminopyridine was added with vigorous stirring, and then 8.22 ml of triethylamine was slowly dropped to be heated and refluxed for 3 hours, while the external temperature was maintained at 80°-90° C.

On completion of the reaction, benzene and triethylamine were eliminated under reduced pressure to obtain 37.7 g of 2-(2',4',6'-trichlorophenoxy)-N-(2'-pyridinyl)-acetamide as a raw reaction product. The above reaction product was recrystallized with 100 ml of cyclohexane to obtain 32.9 g of 2-(2',4',6'-trichlorophenoxy)-N-(2'-pyridinyl)-acetamide as a target product.

The yield of the target compound in relation to 2,4,6-trichlorophenoxyacetyl chloride consumed was 84 percent. Its melting point was 179°-181° C.

Nucleic magnetic resonance spectrum: (CDCl$_3$), ($\delta$=ppm), $\delta$9.17(broad NH), $\delta$7.01-8.33(m), $\delta$4.50(s).

Infrared absorption spectrum: (KBr disc), (cm$^{-1}$), 3100 (NH stretching), 1680.

EXAMPLE 4

Manufacture of 2-(2',4',6'-trichlorophenoxy)-acet-S-(parapchlorobenzyl)-ester Filling in a dry 250 ml flask respectively 150 ml of anhydrous benzene and 32.45 g (0.12 mol) of 2,4,6-trichlorophenoxyacetyl chloride synthesized in Example 2, the reaction mixture was stirred vigorously with slow dropping of 16.89 ml of 4-chlorobenzyl mercaptan. 23.1 ml of triethylamine was then slowly dropped to be heated and refluxed for 5 hours while the external temperature was maintained at 80°-90° C. When the reaction came to an end, benzene and triethylamine were eliminated under reduced pressure to obtain 39.4 g of 2-(2',4',6'-trichlorophenoxy)-acet-S-(para-chlorobenzyl)-ester as a raw reaction product.

The above reaction product was recrystallized with 100 ml of benzene to obtain 37.14 g of 2-(2',4',6'-trichlorophenoxy)-acet-S-(para-chlorobenzyl)-ester as a target compound.

The yield of the target compound in relation to 2,4,6-trichlorophenoxyacetyl chloride was 87.5 percent.

Nucleic magnetic resonance spectrum: (CDCl$_3$), ($\delta$=ppm), $\delta$7.05-8.50(m), $\delta$4.50(s).

EXAMPLE 5

Manufacture of 2,3-dichlorophenoxyacetic acid

Respectively 26.92 g (0.673 mol) of sodium hydroxide and 26.92 g (0.307 mol) of 2,3-dichlorophenol were added to 450 ml of water for dissolution at normal temperature. 28.76 g (0.306 mol) of monochloroacetic acid was further added hereto to be heated and refluxed for 7 hours with the external temperature maintained at 120°-130° C.

When treated as in Example 1 on completion of the reaction, 59.89 g of 2,3-dichlorophenoxyacetic acid was obtained as a raw reaction product.

The yield of the target compound in relation to 2,3-dichlorophenol consumed was 88.3 percent. Its melting point was 173°-175° C.

Nucleic magnetic resonance spectrum (CDCl$_3$+DMSO-d$_6$, 60 MHz), $\delta$6.7-7.3, $\delta$4.7.

EXAMPLE 6

Manufacture of 2,3-dichlorophenoxy-acetyl chloride

After filling in a dry 250 ml flask respectively 59.89 g (0.271 mol) of 2,3-dichlorophenoxyacetic acid synthesized in Example 5 and 79.1 ml (1.084 mol) of thionyl chloride, the reaction mixture was then heated and refluxed for 4-5 hours. When treated as in Example 2 on completion of the reaction, 60.93 g of 2,3-dichlorophenoxyacetyl chloride was obtained as a raw reaction product.

The yield was 94.5 percent. The above compound requires to be completely sealed for use in the subsequent reaction.

EXAMPLE 7

Manufacture of 2-(2',3'-dichlorophenoxy)-N-(2'-pyridinyl)-acetamide

After filling in a dry 500 ml flask respectively 30.47 g (0.128 mol) of 2,3-dichlorophenoxyacetyl chloride synthesized in Example 6 and 250 ml of anhydrous benzene was added with vigorous stirring, and then 8.92 ml of triethylamine was slowly dropped to be heated and refluxed for 2-3 hours, while the external temperature was maintained at 85°-90° C.

When treated as in Example 3 on completion of the reaction, 32.04 g of 2-(2',3'-dichlorophenoxyacet)-N-(2'-pyridinyl) acetamide was obtained as a raw reaction product. The above reaction product was recrystallized with 150 ml of cyclohexane to obtain 30.5 g of 2-(2',3'-dichlorophenoxy)-N-(2-pyridinyl) acetamide as a target product.

The yield of the target compound in relation to 2,3-dichlorophenoxyacetyl chloride consumed was 80.2 percent.

Nucleic magnetic resonance spectrum: (CDCl$_3$), ($\delta$=ppm), $\delta$9.07(broad NH), $\delta$6.6-8.5(m), $\delta$4.65(s).

Infrared absorption spectrum: (NaCl), (cm$^{-1}$), 3080(NH strecting), 1655(C=O).

EXAMPLE 8

Manufacture of 2-(2',3'-dichlorophenoxy)acet-S-(para-chlorobenzyl)-ester

Filling in a dry 500 ml flask respectively 250 ml of anhydrous benzene and 30.46 g (0.128 mol) of 2,3-dichlorophenoxyacetyl chloride synthesized in Example 6, the reaction mixture was stirred vigorously with slow dropping of 16.9 ml of 4-chlorobenzyl mercaptan. 19.83 ml of triethylamine was then slowly dropped to be heated and refluxed for 5-6 hours.

When treated as in Example 4 on completion of the reaction, 43.9 g of 2-(2',3'-dichlorophenoxy)-S-(para-chlorobenzyl)-thioester was obtained as a raw reaction product.

The above reaction product was recrystallized with 100 ml of benzene to obtain 41.1 g of 2-(2',3'-dichlorophenoxy)-acet-S-(para-chlorobenzyl)-ester being a white crystalline as a target compound.

The yield of the target compound in relation to 2,3-dichlorophenoxyacetyl chloride consumed was 89.2 percent.

Melting point: 95°-96° C.

Nucleic magnetic resonance spectrum: (CDCl$_3$), ($\delta$=ppm), $\delta$7.10-8.60(m), $\delta$4.65(s).

EXAMPLE 9

Manufacture of 2,6-dichlorophenoxyacetic acid 30.25 g (0.765 mol) of sodium hydroxide and 56.01 g of 2,6-dichlorophenol were respectively added to 450 ml of water for dissolution at normal temperature. Adding 32.34 g (0.344 mol) of monochloroacetic acid hereto, the reaction mixture was heated and refluxed for 12 hours, while the external temperature was maintained at 110°-120° C.

When treated as in Example 1 on completion of the reaction, 68.45 g of 2,6-dichlorophenoxyacetic acid being a white crystalline as a target compound.

The yield of the target compound in relation to 2,6-dichlorophenol consumed was 85.8 percent.

Melting point: 130°-135° C.

Nucleic magnetic resonance spectrum: (CDCl$_3$), ($\delta$=ppm), $\delta$7.1-7.6(m), $\delta$4.6(s).

EXAMPLE 10

Manufacture of 2,6-dichlorophenoxyacetyl Chloride

Filling in a dry 250 ml flask respectively 65.28 g (0.295 mol) of 2,6-dichlorophenoxyacetic acid synthesized in Example 9 and 86.2 ml (0.181 mol) of thionyl chloride, the reaction mixture was heated and refluxed for 5-6 hours.

When treated as in Example 2 on completion of the reaction, 64.6 g of 2,6-dichlorophenoxyacetyl chloride was obtained as a raw reaction product.

The yield of the target compount in relation to 2,6-dichlorophenoxyacetic acid consumed was 92 percent.

EXAMPLE 11

Manufacture of 2-(2',6'-dichlorophenoxy)-N-(2'-pyridinyl)-acetamide

After filling in a dry 500 ml flask respectively 250 ml of anhydrous benzene and 32.3 g (0.136 mol) of 2,6-dichlorophenoxyacetyl chloride synthesized in Example 10, 12.8 g (0.136 mol) of 2-aminopyridine was added with vigorous stirring, and then 9.48 ml of triethylamine was slowly dropped to be heated and refluxed for 2-3 hours, while the external temperature was maintained at 85°-95° C.

When treated as in Example 3 on completion of the reaction, 2,6-dichlorophenoxy)-N-(2'-pyridinyl)-acetamide was obtained as a raw reaction product.

The above reaction product was recrystallized with 100 ml of cyclohexane to obtain 32.6 g of 2-(2',6'-dichlorophenoxy)-N-(2'-pyridinile)-acetamide being a needle-like crystalline as a target product.

The yield of the target compound in relation to 2,6-dichlorophenoxyacetyl chloride consumed was 81 percent.

Nucleic magnetic resonance spectrum: (CDCl$_3$), ($\delta$=ppm), $\delta$4.73(s), $\delta$9.3(broad NH), $\delta$6.69-8.43(m).

Infrared absorption spectrum: (NaCl), (cm$^{-1}$), 1680(C=0), 3275(NH).

EXAMPLE 12

Manufacture of 2-(2',6'-dichlorophenoxy)-acet-S-(para-chlorobenzyl)-ester

Filling in a dry 500 ml flask respectively 250 ml of anhydrous benzene and 32.9 g (0.136 mol) of 2,6-dichlorophenoxyacetyl chloride synthesized in Example 10, the reaction mixture was stirred vigorously with slow dropping of 9.92 ml of 4-chlorobenzyl mercaptan. 21.1 ml of triethylamine was then slowly dropped to be heated and refluxed for 5-6 hours.

When treated as in Example 4 on completion of the reaction, 45.3 g of 2-(2',6'-dichlorophenoxy)-acet-S-(para-chlorobenzyl)-ester was obtained as a raw reaction product.

The yield of the target compound in relation to 2,6-dichlorophenoxyacetyl chloride consumed was 92.5 percent.

Nucleic magnetic resonance spectrum: (CDCl$_3$), ($\delta$=ppm), $\delta$7.07-8.60(m), $\delta$4.62(s).

EXAMPLE 13

Manufacture of 2,4,5-trichlorophenoxyacetic acid

Respectively 26.4 g (0.66 mol) of sodium hydroxide and 59.3 g (0.3 mol) of 2,4,5-trichlorophenol were added to 450 ml of water for dissolution at normal temperature. 28.2 g (0.3 mol) of monochloroacetic acid was further added hereto to be heated and refluxed for 9-10 hours with the external temperature maintained at 115°-125° C.

When treated as in Example 1 on completion of the reaction, 72.7 g of 2,4,5-trichlorophenoxyacetic acid was obtained as a raw reaction product.

The above reaction product was recrystallized with 100 ml of benzene to obtain 65 g of a white crystalline as a target compound.

The yield of the target compound in relation to 2,4,5-trichlorophenol consumed was 85 percent.

Melting point: 162°–165° C.

EXAMPLE 14

Manufacture of 2,4,5-trichlorophenoxyacetyl chloride

Filling in a dry 250 ml flask respectively 65 g (0.254 mol) of 2,4,5-trichlorophenoxyacetic acid synthesized in Example 13 and 75 ml of thionyl chloride, the reaction mixture was heated and refluxed for 5–6 hours.

When treated as in Example 2 on completion of the reaction, 65 g of 2,4,5-trichlorophenoxyacetyl chloride was obtained as a raw reaction product.

The yield of the target compound in relation to 2,4,5-trichlorophenoxyacetic acid consumed was 93 percent. The above compound requireds to be completely sealed for use in the subsequent reaction.

EXAMPLE 15

Manufacture of 2-(2',4',5'-trichlorophenoxy)-N-(2-pyridinyl)-acetamide

After filling in a dry 250 ml flask respectively 150 ml of anhydrous benzene and 32.5 g (0.118 mol) of 2,4,5-trichlorophenoxyacetyl chloride synthesized in Example 14, 11 g (0.118 mol) of 2-aminopyridine was added with vigorous stirring, and then 8.1 ml of triethylamine was slowly dropped to be heated and refluxed for 2–3 hours, while the external temperature was maintained at 80°–90° C.

When treated as in Example 3 on completion of the reaction, 37 g of 2-(2',4',5'-trichlorophenoxy)-N-(2'-pyridinyl)-acetamide was obtained as a raw reaction product.

The above reaction product was recrystallized with 50 ml of cyclohexane to obtain 33 g of 2-(2',4',5'-trichlorophenoxy)-N-(2'-pyridinyl)-acetamide being a white crystalline as a target product.

The yield of the target compound in relation to 2,4,5-trichlorophenoxyacetyl chloride consumed was 84 percent.

Melting point: 182°–183° C.

Nucleic magnetic resonance spectrum: (CDCl$_3$), (=ppm), 4.6(s), 6.5–7.9(m), 8.6(broad NH).

Infrared absorption spectrum: (NaCl), (cm$^{-1}$), 1680(c=O), 3075(NH).

EXAMPLE 16

Manufacture of 2-(2',4',5'-trichlorophenoxy)-acet-S-(para-chlorobenzyl)-ester

Filling in a dry 250 ml flask respectively 150 ml of anhydrous benzene and 33 g (0.128 mol) of 2,4,5-trichlorophenoxyacetyl chloride synthesized in Example 14, the reaction mixture was stirred vigorously with slow dropping of 17 ml of 4-chlorobenzyl mercaptan. 23 ml of triethylamine was then slowly dropped to be heated and refluxed for 5 hours.

When treated as in Example 4 on completion of the reaction 40 g of 2-(2',4',5'-trichlorophenoxy)-S-(parapchlorobenzyl)-ester was obtained as a raw reaction product.

The above reaction product was recrystallized with 50 ml of benzene to obtain 37.2 g of 2-(2',4',5'-trichlorophenoxy)-S-(para-chlorobenzyl)-ester as a target compound.

The yield of the target compound in relation to 2,4,5-trichlorophenoxyacetyl chloride consumed was 88 percent.

Melting point: 97°–98.5° C.

Nucleic magnetic resonance spectrum: (CDCl$_3$), (δ=ppm), δ7.06–8.60(m), δ4.60–4.70(s).

EXAMPLE 17

Manufacture of para-t-butylphenoxyacetic acid

Respectively 450 ml of water, 26.4 g (0.66 mol) of sodium hydroxide and 45 g (0.3 mol) of para-t-butylphenol were full in a three inlet 1 flask to desolve at nomal temperature. 31 g (0.33 mol) of monochloroacetic acid was further added hereto to be heated and refluxed for 10 hours with the external temperature maintained at 120°–135° C.

When treated as in Example 1 on completion of the reaction, 60 g of para-t-butylphenoxyacetic acid was obtained as a raw reaction product.

The above reaction product was recrystallized with 100 ml of benzene to obtain 57.42 g of white crystalline as a target compound.

The yield of the target compound in relation to para-t-butylphenol consumed was 92 percent.

Melting point: 77°–80° C.

Nucleic magnetic resonance spectrum: (CDCl$_3$), (δ=ppm), δ4.5(s), δ1.3(s), δ10.2(broad OH), δ6.8–7.6(m).

Infrared absorption spectrum: (NaCl), (cm$^{-1}$), 1760(c=O), 3400(broad OH).

EXAMPLE 18

Manufacture of para-t-butylphenoxyacetyl chloride

Filling in a dry 250 ml flask respectively 57.42 g (0.276 mol) of para-t-butylphenoxyacetic acid synthesized in Example 17 and 80.5 ml of thionyl chloride, the reaction mixture was heated and refluxed for 5–6 hours.

When treated as in Example 2 on completion of the reaction, 58.8 g of para-t-buthylphenoxyacetyl chloride was obtained as a raw reaction product.

The yield of the target compound in relation to para-t-butylphenoxyacetic acid consumed was 94.2 percent.

EXAMPLE 19

Manufacture of 2-(4'-t-butylphenoxy)-N-(2'-pyridinyl)-acetamide

After filling in a dry 250 ml flask respectively 200 ml of anhydrous benzene and 29.4 g (0.13 mol) of para-t-butylphenoxyacetyl chloride synthesized in Example 18, 12.24 g (0.13 mol) of 2-aminopyridine was added with vigorous stirring, and then 9.1 ml of triethylamine was slowly dropped to be heated and refluxed for 2–3 hours, while the external temperature was maintained at 85°–95° C.

When treated as in Example 3 on completion of the reaction, 33 g of 2-(4'-t-buthylphenoxy)-N-(2'-pyridinyl)-acetamide was obtained as a raw reaction product.

The above reaction product was recrystallized with 100 ml of cyclohexane to obtain 31 g of 2-(4'3-t-butylphenoxy)-N-(2'-pyridinyl)-acetamide being white crystalline as a target product.

The yield of the target compound in relation to para-t-buthylphenoxyacetyl chloride consumed was 84 percent.

Nucleic magnetic resonance spectrum: (CDCl$_3$), ($\delta$=ppm), $\delta$1.3(s), $\delta$4.5(s), $\delta$6.3–8.2(m), $\delta$10.1.

EXAMPLE 20

Manufacture of 2-(4'-t-butylphenoxy)-acet-S-(para-chlorobenzyl)-ester

Filling in a dry 500 ml flask respectively 200 ml of anhydrous benzene and 29.4 g (0.13 mol) of para-t-butylphenoxyacetyl chloride synthesized in Example 18, the reaction mixture was stirred vigorously with slow dropping of 17.2 ml of 4-chlorobenzyl mercaptan. 9.1 ml of triethylamine was then slowly dropped to be heated and refluxed for 5–6 hours.

When treated as in Example 4 on completion of the reaction, 46.1 g of 2-(4'-t-butylphenoxy)-acet-S-(para-chlorobenzyl)-ester was obtained as a raw reaction product.

The above reaction product was recrystallized with 100 ml of benzene to obtain 42.3 g of 2) 4'-t-butylphenoxy)-acet-S-(para-chlorobenzyl)-ester as a target compound.

The yield of the target compound in relation to para-t-butylphenoxyacetyl chloride consumed was 93 percent.

Nucleic magnetic resonance spectrum: (CDCl$_3$), ($\delta$=ppm), $\delta$7.3–8.3(m), $\delta$4.6(s), $\delta$3.5(s).

EXAMPLE 21

Manufacture of 4-bromo-2-chlorophenoxyacetic acid

Respectively 250 ml of water, 8.8 g of sodium hydroxide and 20.7 g (0.1 mol) of 4-bromo-2-chlorophenol were ful in a 250 ml flask to desolve at normal temperature. 10.4 g (0.11 mol) of monochloroacetic acid was further added hereto to be heated and refluxed for 10 hours with interior temperature maintained at 90° C.

When treated as in Example 1 on completion of the reaction, 26.0 g of 4-bromo-2-chlorophenoxyacetic acid was obtained as a raw reaction product.

The above reaction product was recrystallized with 50 ml of benzene to obtain 24.74 g of 4-bromo-2-chlorophenoxyacetic acid as a target compound.

The yield of the target compound in relation to 4-bromo-2-chlorophenol consumed was 93.2 percent.
Melting point: 125°–128° C.

Nucleic magnetic resonance spectrum: (CDCl$_3$), ($\delta$=ppm), $\delta$6.6–7.5(m), $\delta$4.5(s).

EXAMPLE 22

Manufacture of 4-bromo-2-chlorophenoxyacetyl chloride

Filling in a dry 250 ml flask respectively 24.74 g (0.093 mol) of para-t-butylphenoxyacetic acid synthesized in Example 21 and 27.2 ml of thionyl chloride, the reaction mixture was heated and refluxed for 5–6 hours.

When treated as in Example 2 on completion of the reaction, 25.1 g of 4-bromo-2-chlorophenoxyacetyl chloride was obtained as a raw reaction product.

The yield of the target compound in relation to 4-bromo-2-chlorophenoxyacetic acid was 95 percent.

EXAMPLE 23

Manufacture of 2-(4'-bromo-2'-chlorophenoxy)-acet-S-(para-chlorobenzyl)-ester

Filling in a dry 250 ml flask respectively 150 ml of anhydrous benzene and 12.55 g (0.044 mol) of 4-bromo-2-chlorophenoxyacetyl chloride synthesized in Example 22, the reaction mixture was stirred vigorously with slow dropping of 5.8 ml of 4-chlorobenzyl mercaptan. 5.3 ml of triethylamine was then slowly dropped to be heated and refluxed for 5–6 hours with external temperature maintained at 80°–90° C.

When treated as in Example 4 on completion of the reaction, 18 g of 2-(4'-bromo-2'-chlorophenoxy)-acet-S-(para-chlorobenzyl)-ester was obtained as a raw reaction product.

The above reaction product was recrystallized with 50 ml of benzene to obtain 15 g of 2-(4'-bromo-2'-chlorophenoxy)-acet-S-(para-chlorobenzyl)-ester as a target compound.

The yield of the target compound in relation to 4-bromo-2-chlorophenoxyacenyl chloride consumed was 83.9 percent.

Nucleic magnetic resonance spectrum: (CDCl$_3$), ($\delta$=ppm), $\delta$7.30–8.60(m), $\delta$4.60(s).

EXAMPLE 24

Manufacture of 2-(4'-bromo-2'-chlorophenoxy)-N-(2'-pyridinyl)-acetamide

The target compound can be obtained when 4-bromo-2-chlorophenoxyacetyl chloride and 2-aminopyridine are reacted as in Example 36.

Nucleic magnetic resonance spectrum: (CDCl$_3$), ($\delta$=ppm), $\delta$4.50(s), $\delta$6.3–8.3(m).

EXAMPLE 25

Manufacture of 2-(4'-chloro-2'-nitrophenoxy)-N-(2'-pyridinyl)-acetamide

The target compound can be obtained when 4-chloro-2-mitrophenoxyacetyl chloride and 2-aminopyridine are reacted as in Example 3.

Nucleic magnetic resonance spectrum: (CDCl$_3$), ($\delta$=ppm), $\delta$4.50(s), $\delta$6.3–8.4(m).

EXAMPLE 26

Manufacture of 2-(4'-bromo-2',6'-dimethylphenoxy)-N-(5'-chloro-2'-pyridinyl)-acetamide The target compound can be obtained when 4-bromo-2,6-dimethylphenoxy chloride and 2-amino-5-chloropyridine are reacted as in Example 3.

Nucleic magnetic resonance spectrum: (CDCl$_3$), ($\delta$=ppm), $\delta$2.3(s), $\delta$4.50(s), $\delta$7.1–7.2(s).

EXAMPLE 27

Manufacture of 2-(2',4',6'-trichlorophenoxy)-N-(5'-chloro-2'-pyridinyl)-acetamide The target compound can be obtained when 2,4,6-trichlorophenoxyacetyl chloride and 2-amino-5-chloropyridine are reacted as in Example 3.

Nucleic magnetic resonance spectrum: (CDCl$_3$), ($\delta$=ppm), $\delta$4.50(s), $\delta$6.7–7.7(m), $\delta$7.3(s).

EXAMPLE 28

Manufacture of
2-(2',6'-dibromo-4'-methylphenoxy)-N-(5'-chloro-2'-pyridinyl)-acetamide The target compound can be obtained when 2,6-dibro-4-methylphenoxyacetyl chloride and 2-amino-5-chloropyridine are reacted as in Example 3.

Nucleic magnetic resonance spectrum: (CDCl$_3$), ($\delta$=ppm), $\delta$2.3(s), $\delta$4.50(s), $\delta$7.3(s).

EXAMPLE 29

Manufacture of
2-(4'-bromo-2',6'-dimethylphenoxy)-acet-S-propylester

The target compound can be obtained when 4-bromo-2,6-dimethylphenoxyacetyl chloride and 1-propantiol are reacted as in Example 4.

Nucleic magnetic resonance spectrum: (CDCl$_3$), ($\delta$=ppm), $\delta$1.0–2.0(m), $\delta$2.4–2.7(g), $\delta$2.3(s), $\delta$6.6(s).

EXAMPLE 30

Manufacture of
2-(2',6'-dichlorophenoxy)-acet-S-butylester

The target compound can be obtained when 2,6-dichlorophenoxyacetyl chloride and t-butanetiol are reacted as in Example 4.

Nucleic magnetic resonance spectrum: (CDCl$_3$), ($\delta$=ppm), $\delta$1.0–2.0(m), $\delta$2.4–2.8(m), $\delta$6.5–7.3(m).

EXAMPLE 31

Manufacture of
2-(4'-bromo-2',6'-dimethylphenoxy)-N-(2'-pyridinyl)-acetamide

The target compound can be obtained when 4-bromo-2,6-dimethylphenoxyacetyl chloride and 2-aminopyridine are reacted as in Example 3.

Nucleic magnetic resonance spectrum: (CDCl$_3$), ($\delta$=ppm), $\delta$2.3(s), $\delta$4.50(s), $\delta$6.3–8.3(m).

EXAMPLE 32

Manufacture of
2-(2',6'-dibromo-4'-methylphenoxy)-N-(2'-pyridinyl)-acetamide

The target compound can be obtained when 2,6-dibromo-4-methylphenoxyacetyl chloride and 2-aminopyridine are reacted as in Example 3.

Nucleic magnetic resonance spectrum: (CDCl$_3$), ($\delta$=ppm), $\delta$2.3(s), $\delta$4.50(s), $\delta$6.5–8.4(m).

EXAMPLE 33

Manufacture of
2-(2',6'-dibromo-4'-methylphenoxy)-acet-S-(para-chlorobenzyl)-ester The final compound can be obtained when 2,6-dibromo-4-methylphenoxyacetyl chloride and para-chlorobenzyl mercaptan are reacted as in Example 4.

Nucleic magnetic resonance spectrum: (CDCl$_3$), ($\delta$=ppm), $\delta$2.3(s), $\delta$3.50(s), $\delta$4.50(s), $\delta$7.1(s).

EXAMPLE 34

Manufacture of N-(2,5-dichlorophenoxy)acetylethylene urea

After filling in a dry 250 ml flask respectively 200 ml of anhydrous trichloroethylene and 8.6 g of ethylene urea, 24 g of 2,5-dichlorophenoxyacetyl chloride was added with vigorous stirring and then heated and refluxed for 2 hours. On completion of the reaction, it was cold and crystallized, whereby obtaining 23.7 g of the target compound.

Yield: 88%

Nucleic magnetic resonance spectrum: (CDCl$_3$+DMSO-d$_6$), ($\delta$=ppm), $\delta$3.3(s), $\delta$4.7(s), $\delta$6.15, $\delta$6.7–7.2, $\delta$8.2.

EXAMPLE 35

Manufacture of
N-(2-chloro-4-nitrophenoxyacetyl)ethylene urea

The target compound can be obtained when 2-chloro-4-nitrophenoxyacetyl chloride and ethylene urea are reacted as in Example 34.

Nucleic magnetic resonance spectrum: (CDCl$_3$+DMSO-d$_6$) ($\delta$=ppm), $\delta$3.3(s), $\delta$4.5(s), $\delta$7.0–8.2(m).

EXAMPLE 36

Manufacture of
N-(2-chloro-4-nitrophenoxyacetyl)ethylene thiourea

After filling in a dry 500 ml flask respectively 300 ml of anhydrous trichloroethylene and 10.2 g of ethylene thiourea, 25 g of 2-chloro-4-nitrophenoxyacethyl chloride was added with vigorous stirring and then heated and refluxed for 3 hours. On completion of the reaction, it was cold and crystallized, whereby obtaining 24.3 g of the target compound.

Yield: 77%.

Nucleic magnetic resonance spectrum: (CDCl$_3$+DMSO-d$_6$), ($\delta$=ppm), $\delta$3.5(s), $\delta$4.7(s), $\delta$6.9–7.4, $\delta$7.9, $\delta$8.2.

EXAMPLE 37

Manufacture of
N-(2,3-dichlorophenoxyacetyl)-ethylene thiourea

The target compound can be obtained when 2,3-dichlorophenoxyacetyl chloride and ethylene thiourea are reacted as in Example 36.

Nucleic magnetic resonance spectrum: (CDCl$_3$+DMSO-d$_6$), ($\delta$=ppm), $\delta$3.5(s), $\delta$4.5(s), $\delta$6.7–7.2(m).

EXAMPLE 38

Manufacture of
N-(2,6-difluorophenoxyacetyl)-ethylene thiourea

The target compound can be obtained when 2,6-difluorophenoxyacetyl chloride and ethylene thiourea are reacted as in Example 36.

Nucleic magnetic resonance spectrum: (CDCl$_3$+DMSO-d$_6$), ($\delta$=ppm), $\delta$3.5(s), $\delta$4.5(s), $\delta$6.5–7.3(m).

EXAMPLE 39

Manufacture of
N-(3,4,5-trichlorophenoxyacetyl)-thylene thiourea

The target compound can be obtained when 3,4,5-trichlorophenoxyacetyl chloride and ethylene thiourea are reacted as in Example 36.

Nucleic magnetic resonance spectrum: (CDCl$_3$+DMSO-d$_6$), ($\delta$=ppm), $\delta$3.5(s), $\delta$4.50(s), $\delta$6.9–7.0(s).

EXPERIMENTS ON WEED-KILLING ACTIVITY

The following grain seedlings and weeds are set in metallic nurseries (12×8.5×4 inches) filled with greenhouse soils consisting of clay and sand, mushroom soil and peat by one-third each. The pH of the soil is 6.8–7.2.

| Grain seedlings | Weeds |
| --- | --- |
| Wheat | Pigweed |
| Rice | Wild Mustard |
| Field Corn | Bindweed |
| Soybean | Jimsonweed |
| Oat | Crabgrass |
| Grain Sorghum | Velvetleaf |
| Cotton | Morning Glory |
| Alfalfa | Bromegrass |

Dissolved in acetone and water, the compounds synthesized above are aprayed over each nursery at a rate of 80 gallons per acre. The concentration of the solution is adjusted to 16 pounds per acre. Immediately after spraying, an experimental nursery is placed on an aluminum saucer to be sprinkled with water so that the soil in the nursery may be completely drenched. An additional sprinkling is necessary to keep the moisture. Its surface does not need to be sprinkled with water. The nurseries are sprayed with solution within one week after seed-sowing in the preemergence experiment, while the spraying is made 8 to 10 days after seeds are sown in the postemergence experiment. The results are observed for 14 days following the solution spraying. The weed-killing effect is expressed by the following method of 0–10 grades, with non-effect indicated by 0 and complete weed-killing effect by 10.

| | |
| --- | --- |
| 0 | ineffective |
| 1, 2, 3 | slightly effective |
| 4, 5, 6 | Effective halfway |
| 7, 8, 9 | Highly effective (Plants wither soon) |
| 10 | Plants are withered (Complete weed-killing effect) |

In the above, the effect 3 is the maximum value grain seedlings can endure, while the effect 7 is the maximum value permissible for weeds.

1. Compound:
2-(2',3'-dichlorophenoxy)-N-(2'-pyridinyl)-acetamide

| | Injury Rating | |
| --- | --- | --- |
| Plants | Preemergence | Postemergence |
| Wheat | 3 | 0 |
| Rice | 3 | 2 |
| Field Corn | 3 | 2 |
| Soybean | 3 | 2 |
| Oat | 3 | 0 |
| Grain Sorghum | 3 | 0 |
| Cotton | 3 | 0 |
| Alfalfa | 3 | 1 |
| Pigweed | 9 | 10 |
| Wild Mustard | 9 | 10 |
| Bindweed | 9 | 10 |

2. Compound:
2-(2',6'-dichlorophenoxy)-N-(2'-pyridinyl)-acetamide

| | Injury Rating | |
| --- | --- | --- |
| Plants | Preemergence | Postemergence |
| Wheat | 3 | 2 |
| Rice | 3 | 2 |
| Field Corn | 3 | 2 |
| Soybean | 3 | 1 |
| Oat | 3 | 1 |
| Grain Sorghum | 3 | 1 |
| Cotton | 3 | 1 |
| Alfalfa | 4 | 0 |
| Bindweed | 8 | 9 |
| Jimsonweed | 8 | 9 |

3. Compound:
2-(2',4',6'-trichlorophenoxy)-N-(2'-pyridinyl)-acetamide

| | Injury Rating | |
| --- | --- | --- |
| Plants | Preemergence | Postemergence |
| Wheat | 3 | 2 |
| Rice | 3 | 2 |
| Field Corn | 3 | 2 |
| Soybean | 3 | 2 |
| Oat | 3 | 1 |
| Grain Sorghum | 4 | 2 |
| Cotton | 3 | 2 |
| Alfalfa | 3 | 1 |
| Crabgrass | 8 | 9 |
| Velvetloaf | 8 | 9 |
| Morning Glory | 8 | 9 |

4. Compound:
2-(2',4',5'-trichlorophenoxy)-N-(2'-Pyridinyl)-acetamide

| | Injury Rating | |
| --- | --- | --- |
| Plants | Preemergence | Postemergence |
| Wheat | 3 | 0 |
| Rice | 3 | 0 |
| Field Corn | 3 | 0 |
| Soybean | 3 | 0 |
| Oat | 3 | 0 |
| Grain Sorghum | 3 | 0 |
| Cotton | 3 | 0 |
| Alfalfa | 3 | 0 |
| Bromegrass | 9 | 10 |

5. Compound:
2-(4'-bromo-2'-chlorophenoxy)-N-(2'-pyridinyl)-acetamide

| | Injury Rating | |
| --- | --- | --- |
| Plants | Preemergence | Postemergence |
| Wheat | 3 | 1 |
| Rice | 3 | 1 |
| Field Corn | 3 | 1 |
| Soybean | 4 | 2 |
| Oat | 3 | 1 |
| Grain Sorghum | 4 | 1 |
| Cotton | 3 | 0 |
| Alfalfa | 3 | 0 |
| Pigweed | 8 | 9 |
| Wild Mustard | 9 | 9 |
| Jimsonweed | 10 | 10 |

6. Compound:
2-(4',t-buthylphenoxy)-N-(2'-pyridinyl)-acetamide

| Plants | Injury Rating | |
|---|---|---|
| | Preemergence | Postemergence |
| Wheat | 3 | 1 |
| Rice | 3 | 1 |
| Field Corn | 2 | 1 |
| Soybean | 1 | 0 |
| Oat | 0 | 0 |
| Grain Sorghum | 3 | 1 |
| Cotton | 3 | 1 |
| Alfalfa | 4 | 2 |
| Pigweed | 8 | 9 |
| Bindweed | 7 | 8 |

7. Compound:
2-(4'-chloro-2'-nitrophenoxy)-N-(2'-pyridinyl)-acetamide

| Plants | Injury Rating | |
|---|---|---|
| | Preemergence | Postemergence |
| Wheat | 3 | 0 |
| Rice | 3 | 0 |
| Field Corn | 4 | 1 |
| Soybean | 3 | 0 |
| Oat | 3 | 0 |
| Grain Sorghum | 2 | 0 |
| Cotton | 1 | 0 |
| Alfalfa | 3 | 1 |
| Jimsonweed | 8 | 9 |
| Crabgrass | 8 | 9 |
| Velvetleaf | 9 | 10 |

8. Compound:
2-(4'-bromo-2',6'-dimethylphenoxy)-N-(5'-chloro-2'-pyridinyl)-acetamide

| Plants | Injury Rating | |
|---|---|---|
| | Preemergence | Postemergence |
| Wheat | 3 | 2 |
| Rice | 3 | 2 |
| Field Corn | 4 | 3 |
| Soybean | 4 | 3 |
| Oat | 3 | 0 |
| Grain Sorghum | 4 | 2 |
| Cotton | 3 | 1 |
| Alfalfa | 3 | 1 |
| Pigweed | 8 | 8 |
| Wild Mustard | 7 | 8 |

9. Compound:
2-(2',4',6'-trichlorophenoxy)-N-(5'-Chloro-2'-pyridinyl)-acetamide

| Plants | Injury Rating | |
|---|---|---|
| | Preemergence | Postemergence |
| Wheat | 4 | 3 |
| Rice | 3 | 2 |
| Field Corn | 3 | 2 |
| Soybean | 2 | 1 |
| Oat | 3 | 2 |
| Grain Sorghum | 3 | 2 |
| Cotton | 2 | 1 |
| Alfalfa | 3 | 1 |
| Pigweed | 7 | 8 |
| Bindweed | 7 | 8 |
| Jimsonweed | 8 | 8 |

10. Compound:
2-(2',6'-dibromo-4'-methylphenoxy)-N-(5'-Cloro-2'-pyridinyl)-acetamide

| Plants | Injury Rating | |
|---|---|---|
| | Preemergence | Postemergence |
| Wheat | 3 | 1 |
| Rice | 3 | 1 |
| Field Corn | 2 | 0 |
| Soybean | 3 | 1 |
| Oat | 4 | 2 |
| Grain Sorghum | 3 | 0 |
| Cotton | 3 | 1 |
| Alfalfa | 4 | 1 |
| Crabgrass | 7 | 8 |
| Velvetleaf | 8 | 8 |
| Morning Glory | 7 | 8 |

11. Compound:
2-(4'-bromo-2',6'-dimethylphenoxy)acet-S-propylester

| Plants | Injury Rating | |
|---|---|---|
| | Preemergence | Postemergence |
| Wheat | 4 | 2 |
| Rice | 4 | 2 |
| Field Corn | 3 | 1 |
| Soybean | 4 | 2 |
| Oat | 3 | 1 |
| Grain Sorghum | 3 | 1 |
| Cotton | 3 | 1 |
| Alfalfa | 2 | 0 |
| Morning Glory | 7 | 8 |
| Bromegrass | 7 | 8 |

12. Compound:
2-(2',6'-dichlorophenoxy)-acet-S-butylester

| Plants | Injury Rating | |
|---|---|---|
| | Preemergence | Postemergence |
| Wheat | 3 | 0 |
| Rice | 3 | 0 |
| Field Corn | 3 | 0 |
| Soybean | 3 | 0 |
| Oat | 3 | 0 |
| Grain Sorghum | 3 | 1 |
| Cotton | 3 | 1 |
| Alfalfa | 3 | 1 |
| Pigweed | 8 | 9 |
| Wild Mustard | 9 | 10 |
| Bindweed | 10 | 10 |

13. Compound:
2-(2',6'-dichlorophenoxy)-acet-S-(para-chlorobenzyl)-ester

| Plants | Injury Rating | |
|---|---|---|
| | Preemergence | Postemergence |
| Wheat | 3 | 0 |
| Rice | 3 | 0 |
| Oat | 2 | 0 |
| Grain Sorghum | 4 | 1 |

-continued

13. (continued)

| Plants | Injury Rating | |
|---|---|---|
| | Preemergence | Postemergence |
| Cotton | 3 | 0 |
| Alfalfa | 3 | 0 |
| Jimsonweed | 9 | 9 |
| Crabgrass | 9 | 9 |

14. Compound:
2-(2',4',5'-dichlorophenoxy)-acet-S-(para-chlorobenzyl)-ester

| Plants | Injury Rating | |
|---|---|---|
| | Preemergence | Postemergence |
| Wheat | 3 | 0 |
| Rice | 3 | 0 |
| Field Corn | 2 | 0 |
| Soybean | 3 | 0 |
| Oat | 3 | 0 |
| Grain Sorghum | 3 | 0 |
| Cotton | 2 | 0 |
| Alfalfa | 3 | 0 |
| Pigweed | 9 | 10 |
| Wild Mustard | 9 | 10 |
| Bindweed | 10 | 10 |

15. Compound:
2-(2',3'-dichlorophenoxy)-acet-S-(para-chlorobenzyl)-ester

| Plants | Injury Rating | |
|---|---|---|
| | Preemergence | Postemergence |
| Wheat | 3 | 0 |
| Rice | 3 | 0 |
| Field Corn | 4 | 1 |
| Soybean | 3 | 0 |
| Oat | 3 | 0 |
| Grain Corghum | 3 | 0 |
| Cotton | 2 | 0 |
| Alfalfa | 4 | 2 |
| Pigweed | 8 | 8 |
| Wild Mustard | 7 | 8 |

16. Compound:
2-(4'-t-butylphenoxy)-acet-S-(para-chlorobenzyl)-ester

| Plants | Injury Rating | |
|---|---|---|
| | Preemergence | Postemergence |
| Wheat | 3 | 2 |
| Rice | 3 | 2 |
| Field Corn | 4 | 2 |
| Soybean | 5 | 3 |
| Oat | 3 | 2 |
| Grain Sorghum | 4 | 2 |
| Cotton | 3 | 1 |
| Alfalfa | 4 | 2 |
| Bindweed | 7 | 7 |
| Jimsonweed | 7 | 7 |
| Crabgrass | 7 | 8 |

17. Compound:
2-(4'-bromo-2',6'-dimethylphenoxy)-N-(2'-pyridinyl)-acetamide

| Plants | Injury Rating | |
|---|---|---|
| | Preemergence | Postemergence |
| Wheat | 3 | 0 |
| Rice | 3 | 1 |
| Field Corn | 4 | 1 |
| Soybean | 4 | 1 |
| Oat | 3 | 2 |
| Grain Sorghum | 3 | 3 |
| Cotton | 4 | 1 |
| Alfalfa | 5 | 6 |
| Jimsonweed | 6 | 7 |
| Crabgrass | 7 | 8 |

18. Compound:
2-(2',6'-dibromo-4'-methylphenoxy)-N-(2'-pyridinyl)-acetamide

| Plants | Injury Rating | |
|---|---|---|
| | Preemergence | Postemergence |
| Wheat | 3 | 1 |
| Rice | 3 | 1 |
| Field Corn | 3 | 1 |
| Soybean | 3 | 1 |
| Oat | 3 | 1 |
| Grain Sorghum | 4 | 2 |
| Cotton | 5 | 3 |
| Alfalfa | 3 | 1 |
| Morning Glory | 7 | 8 |
| Crabgrass | 7 | 8 |
| Bromegrass | 8 | 8 |

19. Compound:
2-(2',6'-dibromo-4'-methylphenoxy)-acet-S-(para-chlorobenzyl)-ester

| Plants | Injury Rating | |
|---|---|---|
| | Preemergence | Postemergence |
| Wheat | 3 | 2 |
| Rice | 3 | 2 |
| Field Corn | 4 | 3 |
| Soybean | 4 | 3 |
| Oat | 3 | 2 |
| Grain Sorghum | 2 | 1 |
| Cotton | 5 | 2 |
| Alfalfa | 3 | 1 |
| Pigweed | 7 | 8 |
| Wild Mustard | 7 | 8 |

20. Compound:
2-(2',4',6'-trichlorophenoxy)-acet-S-(para-Chlorobenzyl)-ester

| Plants | Injury Rating | |
|---|---|---|
| | Preemergence | Postemergence |
| Wheat | 3 | 1 |
| Rice | 3 | 1 |
| Field Corn | 3 | 1 |
| Soybean | 3 | 1 |
| Oat | 2 | 0 |
| Grain Sorghum | 4 | 2 |
| Cotton | 4 | 2 |
| Alfalfa | 4 | 2 |
| Bindweed | 7 | 8 |

21. Compound:
N-(2,5-dichlorophenoxyacetyl)-ethylene urea

| Plants | Injury Rating | |
|---|---|---|
| | Preemergence | Postemergence |
| Wheat | 4 | 1 |
| Rice | 3 | 1 |
| Field Corn | 3 | 1 |
| Soybean | 3 | 2 |
| Oat | 2 | 2 |
| Grain Sorghum | 2 | 1 |
| Cotton | 4 | 2 |
| Alfalfa | 3 | 1 |
| Crabgrass | 8 | 8 |
| Velvetleaf | 8 | 8 |

22. Compound:
N-(2-chloro-4-nitrophenoxyacetyl)-ethylene urea

| Plants | Injury Rating | |
|---|---|---|
| | Preemergence | Postemergence |
| Wheat | 4 | 2 |
| Rice | 4 | 2 |
| Field Corn | 4 | 2 |
| Soybean | 4 | 2 |
| Oat | 4 | 2 |
| Grain Sorghum | 4 | 2 |
| Cotton | 5 | 3 |
| Alfalfa | 5 | 6 |
| Morning Glory | 6 | 8 |
| Bromegrass | 7 | 7 |
| Pigweed | 7 | 8 |

23. Compound:
N-(2-Chloro-4-nitrophenoxyacetyl)-ethylene thiourea

| Plants | Injury Rating | |
|---|---|---|
| | Preemergence | Postemergence |
| Wheat | 4 | 2 |
| Rice | 3 | 1 |
| Field Corn | 4 | 2 |
| Soybean | 4 | 2 |
| Oat | 3 | 1 |
| Grain Sorghum | 4 | 2 |
| Cotton | 5 | 3 |
| Alfalfa | 4 | 3 |
| Pigweed | 7 | 8 |
| Wild Mustard | 7 | 8 |

24. Compound:
N-(2,3-dichlorophenoxyacetyl)-ethylene thiourea

| Plants | Injury Rating | |
|---|---|---|
| | Preemergence | Postemergence |
| Wheat | 3 | 1 |
| Rice | 3 | 1 |
| Field Corn | 4 | 2 |
| Soybean | 3 | 1 |
| Oat | 4 | 2 |
| Grain Sorghum | 3 | 1 |
| Cotton | 2 | 1 |
| Alfalfa | 3 | 2 |
| Bindweed | 8 | 8 |
| Jimsonweed | 7 | 7 |
| Crabgrass | 6 | 7 |

25. Compound:
N-(2,6-difluorophenoxyacetyl)-ethylene thiourea

| Plants | Injury Rating | |
|---|---|---|
| | Preemergence | Postemergence |
| Wheat | 4 | 2 |
| Rice | 4 | 2 |
| Field Corn | 3 | 1 |
| Soybean | 4 | 2 |
| Oat | 3 | 1 |
| Grain Sorghum | 5 | 2 |
| Cotton | 4 | 2 |
| Alfalfa | 3 | 0 |
| Bromegrass | 8 | 8 |

26. Compound:
N-(3,4,5-trichlorophenoxyacetyl)-ethylene thiourea

| Plants | Injury Rating | |
|---|---|---|
| | Preemergence | Postemergence |
| Wheat | 4 | 2 |
| Rice | 4 | 2 |
| Field Corn | 5 | 3 |
| Soybean | 4 | 2 |
| Oat | 3 | 0 |
| Grain Sorghum | 4 | 2 |
| Cotton | 3 | 0 |
| Alfalfa | 3 | 0 |
| Pigweed | 7 | 7 |
| Bromegrass | 7 | 7 |

We claim:

1. A method of controlling undesirable vegetation, comprising applying to the locus where control is desired an herbicidally effective amount of a compound selected from the group consisting of 2-(2',3'-dichlorophenoxy)-N-(2'-pyridinyl)-acetamide, 2-(2',6'-dichlorophenoxy)-N-(2'-pyridinyl)-acetamide, 2-(2',4',6'-trichlorophenoxy)-N-(2'-pyridinyl)-acetamide, 2-(2',4',5'-trichlorophenoxy)-N-(2'-pyridinyl))-acetamide, 2-(4'-bromo-2'-chlorophenoxy)-N-(2'-pyridinyl)-acetamide, 2-(4'-t-butylphenoxy)-N-(2'-pyridinyl)-acetamide, 2-(4'-chloro-2'-nitrophenoxy)-N-(2'-pyridinyl)-acetamide, 2-(4'-bromo-2',6'-dimethylphenoxy)-N-(5'-chloro-2'-pyridinyl)-acetamide, 2-(2',4',6'-trichlorophenoxy)-N-(5'-chloro-2'-pyridinyl)-acetamide, 2-(2',6'-dibromo-4'-methylphenoxy)-N-(5'-chloro-5'-pyridinyl)-acetamide, [2-(4'-bromo-2',6'-dimethylphenoxy)-acet-S-propylester, 2-(2',6'-dichlorophenoxy)-acet-S-butylester, 2-(2',6'-dichlorophenoxy)-acet-S-(p-chlorobenzyl)ester, 2-(2',4',5'-trichlorophenoxy)-acet-S-(p-chlorobenzyl)ester, 2-(2',3'-dichlorophenoxy)-acet-S-(p-chlorobenzyl)ester, 2-(4'-t-butylphenoxy)-acet-S-(p-chlorobenzyl)ester,]2-(4'-bromo-2',6'-dimethylphenoxy)-N-(2'-pyridinyl)-acetamide, 2-(2',6'-dibromo-4'-methylphenoxy)-N-(2'-pyridinyl)-acetamide, [2-(2',6'-dibromo-4'-methylphenoxy)-acet-S-(p-chlorobenzyl)ester, 2-(2',4',6'-trichlorophenoxy)-acet-S-(p-chlorobenzyl)ester,]N-(2-chloro-4-nitrophenoxyacetyl)-ethylene thiourea, N-(2,3-dichlorophenoxyacetyl)-ethylene thiourea, N-(2,6-difluorophenoxyacetyl)-ethylene thiourea, and N-(3,4,5-trichlorophenoxyacetyl)-ethylene thiourea.

2. A method in accordance with claim 1 in which said compound is a member selected from the group consisting of 2-(2',3'-dichlorophenoxy)-N-(2'-pyridinyl)-acetamide, 2-(2',6'-dichlorophenoxy)-N-(2'-pyridinyl)-acetamide, 2-(2',4',6'-trichlorophenoxy)-N-(2'-pyridinyl)-acetamide, 2-(2',4',5'-trichlorophenoxy)-N-(2'-pyridinyl)-acetamide, 2-(4'-bromo-2'-chlorophenoxy)-N-(2'-pyridinyl)-acetamide, 2-(4'-t-butylphenoxy)-N-(2'-pyridinyl)-acetamide, 2-(4'-chloro-2'-nitrophenoxy)-N-(2'-pyridinyl)-acetamide, 2-(4'-bromo-2',6'-dimethylphenoxy)-N-(2'-pyridinyl)-acetamide, 2-(2',6'-dibromo-4'-methylphenoxy)-N-(2'-pyridinyl)-acetamide, N-(2-chloro-4-nitrophenoxyacteyl)-ethylene thiourea, N-(2,3-dichlorophenoxyacetyl)-ethylene thiourea, N-(2,6-difluorophenoxyacetyl)-ethylene thiourea, and N-(3,4,5-trichlorophenoxyacetyl)-ethylene thiourea.

3. A method in accordance with claim 1 comprising applying said compound postemergence to said undesirable vegetation.

* * * * *